United States Patent [19]

Kanatani

[11] 4,313,446
[45] Feb. 2, 1982

[54] STEEL WIRE PRESSURE AESTHESIOMETER

[75] Inventor: Frank N. Kanatani, Baton Rouge, La.

[73] Assignee: The United States of America as represented by the Secretary of the Department of Health, Education and Welfare, Washington, D.C.

[21] Appl. No.: 129,982

[22] Filed: Mar. 11, 1980

[51] Int. Cl.³ .............................................. A61B 5/10
[52] U.S. Cl. ..................................... 128/744; 128/740
[58] Field of Search ............. 33/174 D, 174 B, 169 B, 33/169 R; 73/379, 141 R; 116/DIG. 6, 319, 320; 128/744, 740

[56] References Cited

U.S. PATENT DOCUMENTS

| 1,245,130 | 10/1917 | Somers | 33/169 R |
| 2,974,416 | 3/1961 | Nurcher | 33/169 R |
| 4,250,891 | 2/1981 | Carlson et al. | 128/744 |

OTHER PUBLICATIONS

Block's Aesthesiometer, Cat. #18011, Stoelting & Co. Catalogue, 1930.

Primary Examiner—Robert W. Michell
Assistant Examiner—Nancy A. B. Swisher
Attorney, Agent, or Firm—Browdy and Neimark

[57] ABSTRACT

An aesthesiometer consisting of an elongated length-calibrated support bar with a handle at one end. The bar has a longitudinal groove communicating with a hole near the other end of the bar. A steel wire is fastened to the handle and lies in the groove, the wire having a right-angled bend forming a depending skin probe arm which extends through the hole. An adjustable wire-retaining block is slidably engaged on the support bar and has a flange depending into the groove and holding down the wire, thus regulating the length of the flexible portion of the wire and thus controlling the effective stiffness of the flexible portion. The upward deflection of the right-angled bend is read quantitatively on an arcuate concentric series of scale lines on a scale card attached to the free end of the support bar. The deflection readings relative to the arcuate scale lines and the longitudinal position settings of the wire-retaining block on the support bar are used in conjunction with a top loading balance platform scale to form calibration curves to measure the stress on a skin area of the patient in terms of the readings obtained from the deflection scale and the longitudinally set positions of the wire-retaining block on the support bar.

16 Claims, 12 Drawing Figures

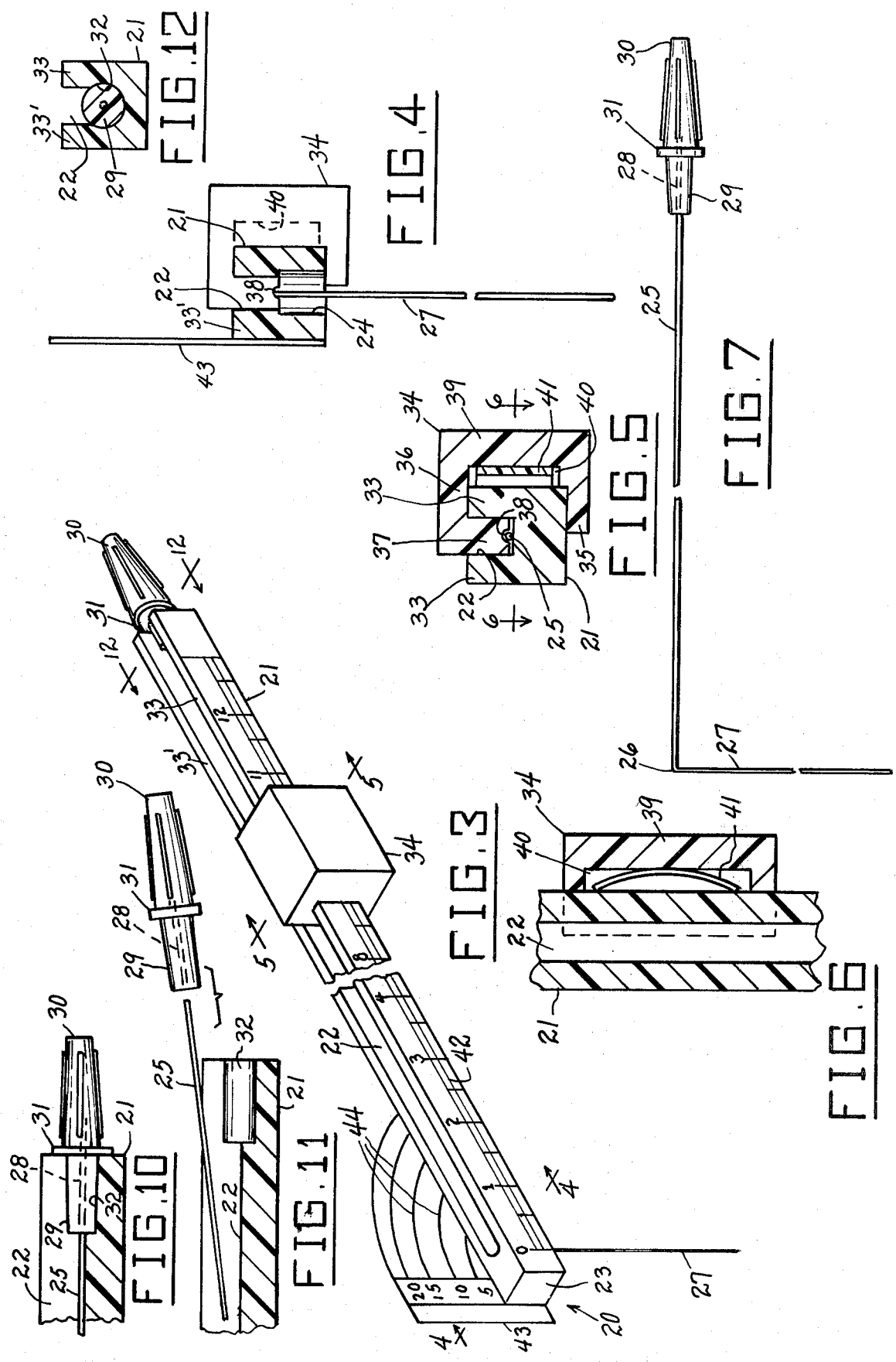

STEEL WIRE PRESSURE AESTHESIOMETER

FIELD OF THE INVENTION

This invention relates to neurological test apparatus, and more particularly to sensory response testing equipment for use in the assessment of abnormal sensory patterns such as those associated with leprosy neuritis and similar diseases.

BACKGROUND OF THE INVENTION

Sensory responses of patients suffering from diseases such as leprosy neuritis (associated with Hansen's Disease), and similar diseases, have been tested in various ways. For example, in making motor response tests, measure of strength of pinch "pinchometers" and grasp "dynamometers", as well as "Voluntary Muscle Testers" have been used. Another previously employed method of assessing results of treatment of leprosy neuritis has been by testing sensory response by subjecting a skin area of a patient to contact by a cotton tip, a feather, a pin, a hair, or a nylon filament.

A typical well known prior method of making detailed sensory response tests has been by using a Weinstein-Semmes nylon filament pressure aesthesiometer, shown for example in FIG. 1. This has become a fairly popular sensory testing tool because of its mechanical simplicity and because it can be clinically standardized for use in roughly assessing nerve damage changes. However, it is subject to a number of serious disadvantages.

For testing over a reasonable range of sensory conditions, a relatively large number of suitably calibrated Weinstein-Semmes pressure aesthesiometers are required. For example, to cover a range of sensed stress values (gm/sq.mm) from about 20 gm/sq.mm to 170 gm/sq.mm, a typical set would consist of 11 aesthesiometers, each being calibrated to allow its filament to buckle at a designated value of stress along said range. The manufacturer provides markings M on the handle of the aesthesiometer to indicate a designated function of the measured buckling force F, wherein $M = \log (10 \times F)$ The following table shows the force measurements, stress and M calculations for a typical set of Weinstein-Semmes pressure aesthesiometers:

TABLE I

| Manufacturers Marking M | M,Calculated from Measured Force | Measured Force F(gm) | Area A(sq.mm) | Measured Stress S = gm/sq.mm |
|---|---|---|---|---|
| 6.10 | 5.94 | 86.5 | 0.51 | 171 |
| 5.88 | 5.86 | 73.2 | 0.42 | 175 |
| 5.46 | 5.35 | 22.3 | 0.27 | 82.0 |
| 5.18 | 5.27 | 18.6 | 0.22 | 84.9 |
| 5.07 | 5.23 | 17.0 | 0.18 | 94.9 |
| 4.93 | 5.03 | 10.6 | 0.14 | 76.1 |
| 4.74 | 4.50 | 3.14 | 0.081 | 38.9 |
| 4.56 | 4.45 | 2.81 | 0.077 | 36.6 |
| 4.31 | 4.27 | 1.85 | 0.063 | 29.5 |
| 4.17 | 4.20 | 1.58 | 0.047 | 33.7 |
| 4.08 | 3.99 | 0.977 | 0.041 | 23.9 |

The above data appears in Levin, S. et al, "Von Frey's Method of Measuring Pressure Sensibility in the Hand: An Engineering Analysis of the Weinstein-Semmes Pressure Aesthesiometer", Journal of Hand Surgery, Vol. 3, No. 3, May 1978, pp 211–216.

The term "stress" is defined as a function of the resultant internal force (reaction) that resists changes in the size or shape of a body acted on by external forces; "stress" in the nylon filament is the ratio of applied load to the corresponding cross-sectional area. Therefore, the "stress" will be the same as the pressure on the surface of the skin, wherein the contact area is equal to the cross-sectional area of the filament.

It will be noted that in using a set of Weinstein-Semmes aesthesiometers, a number of aesthesiometers must be used in order to locate the one which buckles at the minimum stress value at which the patient senses the applied pressure. This may require the handling of a substantial number of aesthesiometers before the appropriate aesthesiometer is located.

It was found that in a typical set of manufactured Weinstein-Semmes aesthesiometers the shapes of the ends of the nylon filaments were not uniform, some being flared, some being cut at a slant, producing a sharp point, and some having frayed ends. A frayed end has more area in contact with the skin than the area corresponding to the measured diameter of the associated filament. A sharp point on the end of a filament would elicit a response like that of a pinprick, rather than that obtained from contact with a flat filament face.

Thus, with a set of Weinstein-Semmes aesthesiometers, the ends of the filaments would need to be uniformly cut cleanly with a flat face, for valid measurements for stress computation and for sensory response characteristics consistent with actual filament cross-sectional area.

Therefore, there is a definite need for an improved aesthesiometer which avoids the above-described disadvantages and inconveniences inherent in the previously used devices.

SUMMARY OF THE INVENTION

Accordingly, an object of the invention is to provide for improved testing of sensory response; and another object is to provide a novel and improved aesthesiometer which overcomes the disadvantages, shortcomings and deficiencies of the previously employed aesthesiometers.

A further object of the invention is to provide an improved aesthesiometer which employs a steel wire as a pressure-delivering element in place of the nylon filament previously employed.

A still further object of the invention is to provide an improved aesthesiometer which enables a wide range of specified pressures to be delivered to a skin area under test.

A still further object of the invention is to provide an improved aesthesiometer which can be set so that its skin contact element can be easily adjusted in stiffness, whereby to provide a desired degree of compliance, and so that the aesthesiometer can be employed over a wide range of skin pressures.

A still further object of the invention is to provide an improved aesthesiometer having a deflection scale which shows the amount of deflection of its skin-contacting element and which enables the stress generated thereby to be readily determined.

A still further object of the invention is to provide an improved aesthesiometer having a resilient deflection arm and having an adjustable slide block engageable with said arm to adjust the effective stiffness thereof and to greatly extend the working range of stress values obtainable with patients being tested for sensory response.

A still further object of the invention is to provide an improved aesthesiometer which has inherent wide-range testing capability and which can be used to assess patient sensory response over a wide range of stress values, the aesthesiometer being self-contained, being easy to adjust for a specific desired stress value range, and being easily readable to determine deflection values of its skin contact member, from which actual stress conditions in the contact area can be readily determined.

A still further object of the invention is to provide an improved aesthesiometer which is durable in construction, which can be accurately set to repeat previous settings, which has practically unlimited shelf life, and which avoids fatigue of its probe element.

A still further object of the invention is to provide an improved aesthesiometer which has a resilient deflection arm which will return to its initial configuration after each test trial, even after repeated test trials.

A still further object of the invention is to provide an improved aesthesiometer which has as few as three different changeable progressively-sized steel wire deflection members which may be employed to cover the complete range of force values available from about 20 nylon filaments employed in previous aesthesiometers, and wherein the stiffness of the steel wire deflection arms can be preset to allow a desired spectrum of force values to be obtained, the force value ranges of the changeable wire members overlapping to allow cross-checking of sensory responses, such cross-checking being impossible with previously employed nylon filament aesthesiometer sets.

A still further object of the invention is to provide an improved aesthesiometer which employs changeable different size steel wire deflection members and wherein it is easy to change said steel wire deflection members when desired.

A still further object of the invention is to provide an improved aesthesiometer which is not affected by temperature changes within any range of ambient temperature to which patients would normally be exposed for sensory testing.

BRIEF DESCRIPTION OF THE DRAWINGS

Further objects and advantages of the invention will become apparent from the following description and claims, and from the accompanying drawings, wherein:

FIG. 3 is an enlarged fragmentary perspective view of the aesthesiometer of FIG. 2.

FIG. 4 is an enlarged transverse vertical cross-sectional view taken substantially on line 4—4 of FIG. 3.

FIG. 5 is an enlarged transverse vertical cross-sectional view taken substantially on line 5—5 of FIG. 3.

FIG. 6 is a fragmentary horizontal cross-sectional view taken substantially on line 6—6 of FIG. 5.

FIG. 7 is an enlarged fragmentary side elevational view of a steel wire probe and handle as employed in the aesthesiometer of FIGS. 2 to 6.

FIG. 10 is an enlarged fragmentary vertical longitudinal cross-sectional view of the aesthesiometer of FIGS. 2 to 7, taken at its handle end portion.

FIG. 11 is a longitudinal vertical cross-sectional view similar to FIG. 10, showing the removal of the handle during the process of changing the aesthesiometer steel probe wire.

FIG. 12 is an enlarged transverse vertical cross-sectional view taken substantially on line 12—12 of FIG. 3.

DESCRIPTION OF A PREFERRED EMBODIMENT

Figure 1:
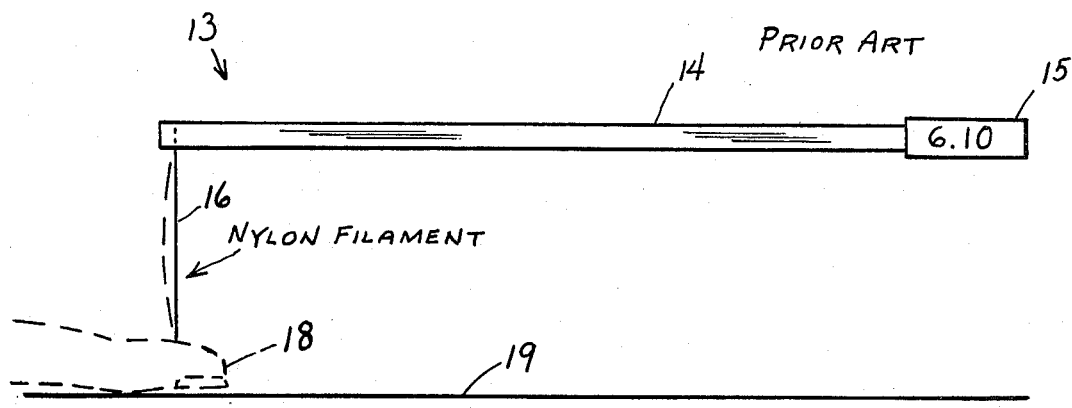
FIG. 1 is an elevational view of an aesthesiometer of the prior art employing a nylon filament as the skin probe.

Referring to the drawings, FIG. 1 illustrates a typical prior art aesthesiometer 13, of the Weinstein-Semmes type, comprising an elongated rod member 14 provided with a handle portion 15 at one end and a nylon filament 16 perpendicularly secured at the other end. The aesthesiometer is calibrated so that the nylon filament 16 will begin to deflect laterally and then buckle, responsive to a predetermined reactive force developed at its tip, said reactive force being found by actual measurement, for example, by employing a conventional top loading, force-indicating balance such as that illustrated at 17 in FIG. 8. The manufacturer provides M-value markings on the handle 15, wherein $M = \log(10 \times F)$, wherein F is the buckling force in milligrams. If the diameter of the filament 16 is measured, the cross-sectional area may be calculated, and the stress value may then be computed by dividing F by said area. Buckling stress data for a typical set of nylon-filament aesthesiometers may be provided by a listing such as appears in Table I above. In using the Weinstein-Semmes aesthesiometers 13 they may be systematically sequentially applied to a finger 18, or other skin area of the patient whose sensitivity is to be examined, using the handles 15 for holding the aesthesiometers and for applying force thereto. Ultimately one aesthesiometer will be found with which the patient recognizes a clear sensation at the tested skin area at a level of applied force sufficient to cause its nylon filament to buckle. The degree of stress at the tested area (S=F/area) can then be determined from the M number on the handle of said aesthesiometer by referring to an M-calibration listing similar to Table I.

As shown in FIG. 1, in making the test on a patient's finger 18, the finger may be placed on a flat surface 19, facing upwardly, and the aesthesiometer handle 15 is held by the examiner with the filament tip in a depending position and engaged on the finger. Force is then applied to urge the filament downwardly so as to develop reactive stress in the finger. If the patient senses the stress at the point wherein the filament 16 begins to buckle, the M-value on the aesthesiometer gives a measure of the sensed pressure.

Obviously, a relatively large number of nylon filament aesthesiometers will be required to usefully test a patient over a reasonably wide range of generated reactive stress values, since each aesthesiometer 13 can provide a reading of only a single stress test point.

Referring to FIGS. 2 to 7, 20 generally designates a typical improved aesthesiometer according to the present invention. The aesthesiometer 20 comprises an elongated support bar 21 of generally rectangular cross sectional shape formed with a longitudinal top groove 22 terminating adjacent to the forward end 23 of bar 21, the end of the groove being in registry with a circular aperture 24 extending through the bottom wall of said groove, as shown in FIG. 4. An elongated resilient steel wire rod 25 is disposed in groove 22, said wire rod being formed with a right-angled bend 26 to define a depending arm 27 which normally extends substantially coaxially through the aperture 24. At its rear end the flexible wire rod 25 is frictionally tightly secured in an axial bore 28 formed in the reduced slightly tapering shank portion 29 of a handle member 30 (see FIG. 7) but is at times detachable therefrom, as will be presently described. Handle member 30 is integrally formed with a stop collar portion 31 adjacent to shank portion 29.

The shank portion 29 is frictionally secured in the rear end portion of bar member 21 with a snap fit, the bar member being formed with a shank-receiving socket 32 (see FIG. 12) into which said shank portion may be downwardly pressed. Bar member 21 is formed from suitable yieldable material, such as molded plastic material, so that the spaced vertical flanges 33, 33' at the opposite sides of groove 22 are sufficiently resiliently yieldable to admit shank portion 29 into socket 32 and to allow removal of the shank portion at times, for example, to change the wire rod, as will be presently described.

Designated at 34 is a generally C-shaped slide block slidably engaged around the bar flange 33 and having a horizontal bottom arm 35 engaged beneath bar 21 and a top arm 36 extending over the top edge of said bar flange 33 and being formed with a depending flange 37 slidably engaged in groove 22, as shown in FIG. 5. The bottom edge of flange 37 is formed with a downwardly facing longitudinal guide groove 38 slidably receiving the wire rod 25 and holding said wire rod against the floor of groove 22. The vertical wall 39 of block 34 is formed with an internal rectangular recess 40 in which is disposed an arcuately bowed leaf spring 41 exerting frictional holding force on bar 21, as shown in FIG. 6.

The vertical external face of bar flange 33 is inscribed with a block positioning scale 42, which may be marked off in centimeters or other desired length units. At its forward end the bar 21 is provided with a vertical deflection scale card 43, which is rigidly secured to the vertical external face of bar flange 33' and which is inscribed with a wire deflection scale in the form of a plurality of concentric scale arcs 44 at uniformly spaced radial distances from a transverse zero axis containing the normal rest position of the wire corner bend 26.

Figure 2:
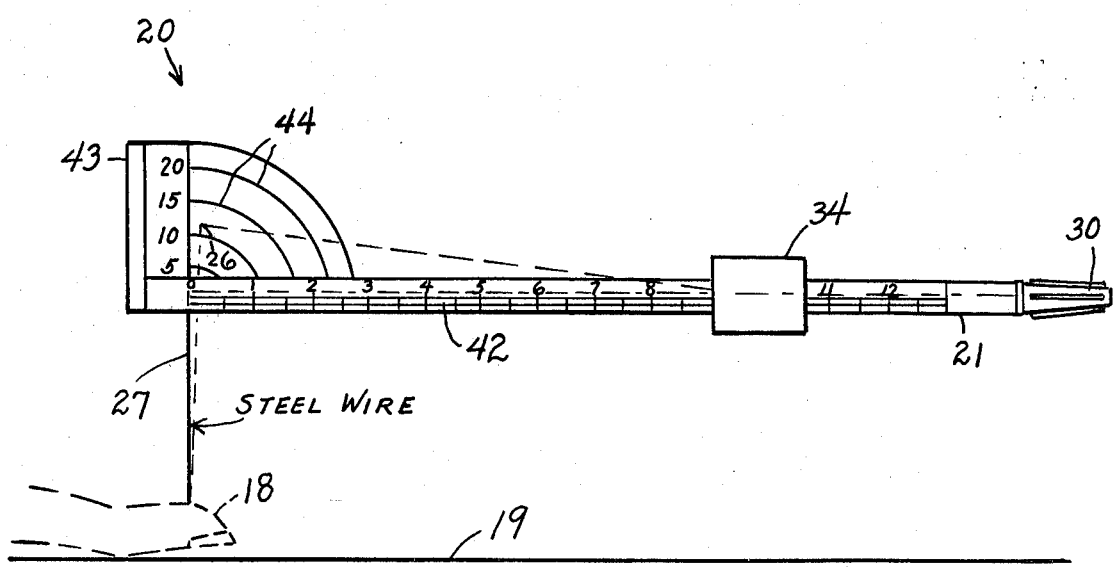
FIG. 2 is a side elevational view of an improved aesthesiometer constructed in accordance with the present invention.

In using the aesthesiometer 20, the flat tip of the depending wire arm 27 is engaged on the patient's finger 18, as in FIG. 2, or on any other skin area to be tested for sensitivity, and the examiner exerts downward force on the handle 30, causing the wire bend 26 to deflect with the steel wire rod 25 to a degree in accordance with the amount of applied downward force. The effective stiffness of the wire rod can be adjusted by setting the block 34 along the scale 42. By suitably calibrating the instrument in a manner presently to be described, the pressure generated on the patient's finger 18, or on another skin area under test, can be determined from the positional setting of block 34 and the degree of deflection of corner bend 36 as read on the deflection scale 43.

Figure 8:
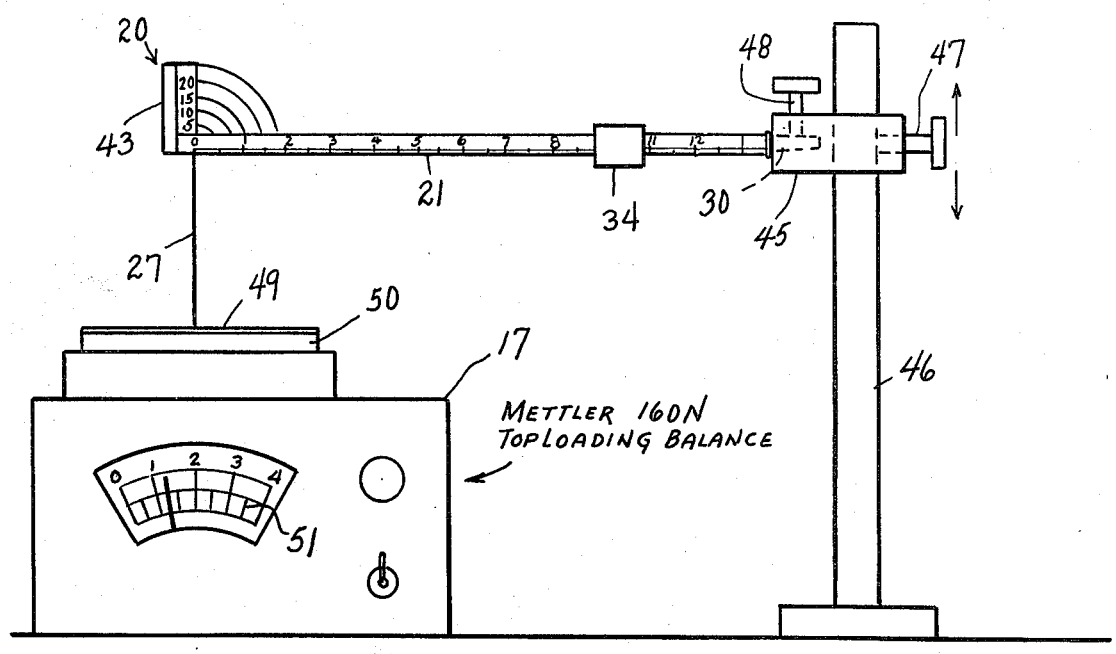
FIG. 8 is a side elevational view of an aesthesiometer of the present invention set up for calibration by means of a conventional top loading balance.
Figure 9:
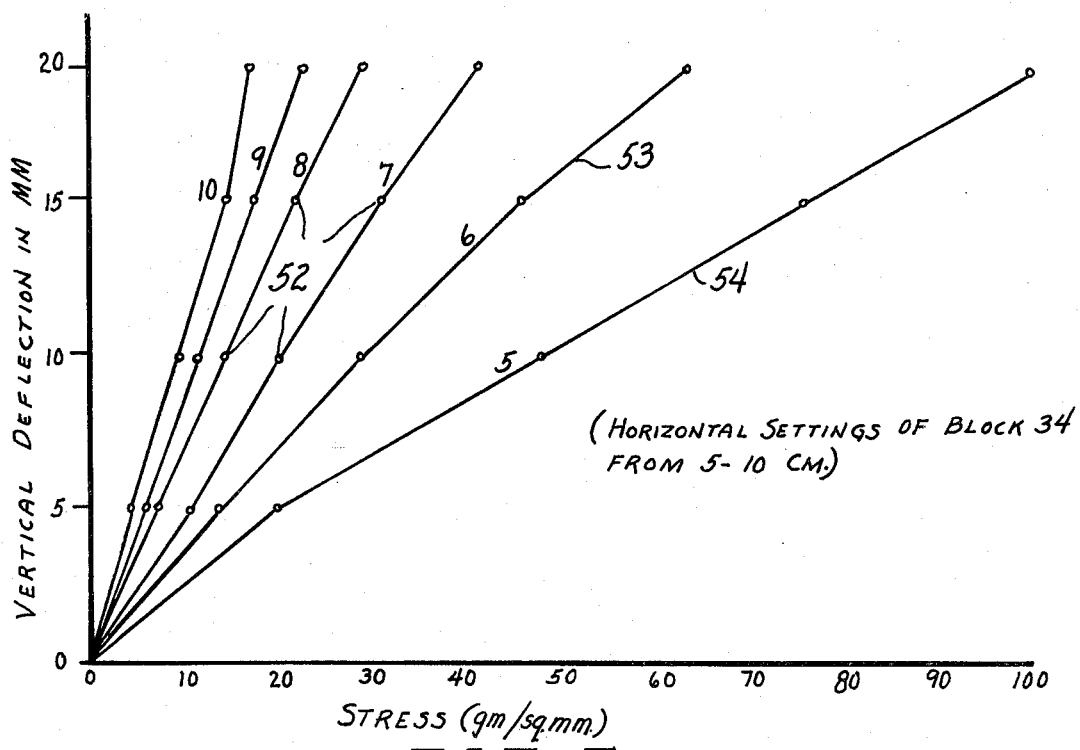
FIG. 9 is a graph showing typical calibration curves obtained from the apparatus of FIG. 8, for various settings of the aesthesiometer slide block.

FIG. 8 illustrates a typical arrangement for calibrating an aesthesiometer 20. The handle portion 30 of the aesthesiometer is horizontally clamped in a vertically adjustable slidable block 45 mounted on a vertical standard or post 46, said block 45 being provided with a set screw 47 for clamping the block 45 in any one of a series of selected heights on the post member 46. The block 45 has a suitable horizontal bore or recess to receive the handle portion 30 and has a set screw 48 to clampingly secure the handle 30, such securement being such that bar 21 extends horizontally and wire element 27 depends vertically. The tip of wire element 27 is engaged on an anti-slip friction pad 49 provided on the horizontal platform 50 of a conventional top loading balance, such as a Mettler 160N top loading balance. Starting from a zero position with the blunt tip of wire element 27 engaging the pad 49, the block 45 is incrementally lowered on post 46, each step in its descent generating a respective force whose value is indicated on the readout scale 51 of the balance 17. Simultaneously with each downward step of the aesthesiometer 20 there is a deflection of the corner bend 26 of the steel wire relative to the deflection scale 43. A series of readings of the force indications on the scale 51 with accompanying deflection readings on the scale card 43 may be taken for each of various selected settings of the adjustable block member 34. This data may be used to plot respective calibration curves for the various selected settings of said block member 34. FIG. 9 shows a group of such calibration curves, the force values being converted into stress, or pressure, values by dividing the measured force readings by the cross-sectional area of the steel wire of the aesthesiometer. For example, the force values shown on balance 17 may be read at the deflections to the respective arcuate lines on card 43 marked "5", "10", "15" and "20". The calculated corresponding stress values may be used as the horizontal coordinates of the respective curve-plotting points 52, whereas the vertical coordinates are the "5", "10", "15" and "20" mm deflections generated on the card 43 by corner bend 26. Thus, a respective calibration curve may be provided for the different selected settings of the block 34, as illustrated in FIG. 9. From such calibration data, for a particular setting of block 34 the stress value corresponding to an observed deflection of the corner bend 26 may be readily found from the calibration curve corresponding to this block setting.

It will be seen from FIG. 9 that some of the calibration curves cover common values of stress, namely, have overlapping range portions. For example, the curve 53 for the 6 cm setting of block 34 covers a stress range from zero to about 63 gm/sq.mm, which is part of the stress range covered by the curve 54 for the 5 cm setting of block 34. This affords an opportunity for cross-checking the stress values observed in the overlapping range by changing from one setting of block 34 to an adjacent setting in making a particular test on a patient, and then noting whether or not the stress values obtained in the two test trials are substantially equal.

The range of applied force values which may be obtained with a given steel wire rod is relatively wide as compared with that obtainable with a reasonable number of nylon filaments 16. It has been found that two or three different-size (gauge) wire rods 25 may be employed to replace the range of force values covered by about 20 nylon filaments. Thus, a different-size wire rod may be substituted for an original wire rod if so desired. FIG. 7 shows a typical subassembly comprising a steel wire rod 25 with its end frictionally held in the bore 28 of a handle member 30 and being detachable therefrom. FIG. 10 shows the normal assembled condition of the parts, with the shank portion 29 tightly held in the socket 32, as in FIG. 12. To remove the original steel wire rod subassembly, the handle 30 may be pulled away from the wire rod 25, disengaging from the socket 32, as shown in FIG. 11. This allows the slide block 34 to be removed, which in turn allows the original wire rod 25 to be disengaged from the support bar 21. The different-size wire rod may then be inserted in the support bar groove 22 with its depending portion 27 engaged through the hole 24, and the slide block 34 may then be replaced on the support bar 21, slidably engaged around the flange 33. The handle 30 of the replacement wire rod 25 may then be forced onto the rear end of the replacement wire rod and its shank portion 29 may then be lockingly engaged in the socket 32.

In detaching and replacing the handle 30, it may be either moved vertically between the yieldable flanges 33, 33' or may be moved axially endwise relative to the associated wire rod 25.

It will be noted that the slide block 34 forms part of the means to secure the non-flexing end portion of the wire member 25 to the support bar 21, and that the guide groove 38 of flange 37 constitutes a longitudinally adjustable flexural fulcrum for the wire member.

Although steel wire has proven to be satisfactory for use as the pressure-responsive deflection element of the aesthesiometer, wires of other metals or materials having similar physical characteristics may be employed, within the spirit of the present invention.

While a specific embodiment of an improved aesthesiometer has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment. For example, the wire 25 may be provided with a plastic sleeve which extends almost to the flat tip of the depending wire arm 27, e.g. suitably to ¾" of the tip.

What is claimed is:

1. An aesthesiometer comprising an elongated substantially rigid support member, a resilient wire member on said support member and extending therealong, means securing one end portion of said wire member to said support member so as to bias the wire member toward the support member, said wire member being formed with a bend at its free end portion to define a depending skin probe arm engageable with a skin area of a patient and to cause a deflection of the bend away from the support member responsive to force applied to the support member with the probe arm in contact with such skin area, means to measure the amount of such deflection, and abutment means adjustably mounted on the support member formed to overlie and abut said wire member at selected locations along its length so as to provide an adjustable fulcrum to vary the effective flexural length of the wire member.

2. The aesthesiometer of claim 1, and wherein said support member is formed with an aperture through which said probe arm extends.

3. The aesthesiometer of claim 1, and wherein said measuring means comprises a scale card member secured to said support member adjacent said bend.

4. The aesthesiometer of claim 1, and wherein said abutment means comprises a block member slidably mounted on the support member and having a wire-retaining element engaging the wire member.

5. The aesthesiometer of claim 4, and a length scale on the support member to indicate the adjusted position of said block member.

6. The aesthesiometer of claim 1, and wherein said elongated support member is formed with a longitudinal groove normally receiving said wire member.

7. The aesthesiometer of claim 6, and wherein said abutment means comprises an adjustable block member slidably engaged on the elongated support member and having a wire-restraining element extending into said groove and engaging said wire member.

8. The aesthesiometer of claim 7, and a longitudinal length scale on the elongated support member to indicate the adjusted position of said block member.

9. The aesthesiometer of claim 1, and wherein said abutment means comprises a wire restraining generally C-shaped block slidably mounted on the support member in a position to limit flexure of the wire member.

10. The aesthesiometer of claim 1, and wherein said deflection-measuring means comprises a scale card member secured on the support member adjacent said bend and parallel to said wire member and being provided with a deflection scale to indicate the amount of deflection of said bend away from the support member responsive to the reaction of the skin area of the patient engaged by the probe arm.

11. The aesthesiometer of claim 10, and wherein said deflection scale has a zero point located adjacent to the rest position of said bend.

12. The aesthesiometer of claim 1, and wherein said support member is formed with a longitudinal groove receiving said wire member, and wherein said wire-abutment means includes a flange portion extending into said groove and engaging the wire member.

13. The aesthesiometer of claim 12, and wherein said support membr is formed with an aperture adjacent the end of the groove, and wherein said probe arm extends through said aperture.

14. The aesthesiometer of claim 1, and wherein said support member is provided with a detachable handle portion, and wherein said wire member is detachably secured to said handle portion.

15. The aesthesiometer of claim 1, and wherein said support member is formed with a longitudinal recess receiving said wire member, and wherein said securing means includes a longitudinally adjustable restraining member slidably retentively engaged on said support member and having a flange portion extending into said recess and formed with a guide groove receiving said wire member and forming a flexural fulcrum for the wire member.

16. The aesthesiometer of claim 1, wherein said resilient wire member is formed of steel.

* * * * *

UNITED STATES PATENT AND TRADEMARK OFFICE
CERTIFICATE OF CORRECTION

PATENT NO. : 4,313,446
DATED : February 2, 1982
INVENTOR(S) : Frank N. KANATANI

It is certified that error appears in the above-identified patent and that said Letters Patent are hereby corrected as shown below:

Claim 15, line 3, "securing" should read --abutment--

Signed and Sealed this

Twenty-ninth Day of June 1982

[SEAL]

Attest:

GERALD J. MOSSINGHOFF

Attesting Officer     Commissioner of Patents and Trademarks